US005479252A

United States Patent [19]
Worster et al.

[11] Patent Number: 5,479,252
[45] Date of Patent: Dec. 26, 1995

[54] LASER IMAGING SYSTEM FOR INSPECTION AND ANALYSIS OF SUB-MICRON PARTICLES

[75] Inventors: Bruce W. Worster, Saratoga; Dale E. Crane; Hans J. Hansen, both of Pleasanton; Christopher R. Fairley, San Jose; Ken K. Lee, Los Altos, all of Calif.

[73] Assignee: Ultrapointe Corporation, San Jose, Calif.

[21] Appl. No.: 80,014

[22] Filed: Jun. 17, 1993

[51] Int. Cl.$^6$ .................................................. G01N 21/88
[52] U.S. Cl. .................... 356/237; 356/369; 250/559.42; 250/559.48
[58] Field of Search ............................... 356/237, 369, 356/317, 445; 250/563, 572

[56] References Cited

U.S. PATENT DOCUMENTS

| | | | |
|---|---|---|---|
| Re. 34,214 | 4/1993 | Carlsson et al. | 358/93 |
| 2,758,502 | 8/1956 | Scott et al. | 356/100 |
| 2,969,708 | 1/1961 | Polanyi et al. | 88/14 |
| 3,013,467 | 12/1961 | Minsky | 88/14 |
| 3,049,047 | 8/1962 | Polanyi et al. | 88/14 |

(List continued on next page.)

FOREIGN PATENT DOCUMENTS

| | | |
|---|---|---|
| 0052892 | 6/1982 | European Pat. Off. . |
| 0112401 | 7/1984 | European Pat. Off. . |
| 0155247 | 9/1985 | European Pat. Off. . |
| 1185839 | 3/1970 | United Kingdom . |
| 2132852 | 7/1984 | United Kingdom . |
| 2152697 | 8/1985 | United Kingdom . |
| 2184321 | 6/1987 | United Kingdom . |
| WO79/01027 | 11/1979 | WIPO . |

OTHER PUBLICATIONS

A. F. Slomba et al., "A Laser Flying Spot Scanner for Use in Automated Fluorescence Antibody Instrumentation," Journal of The Association For The Advancement of Medical Instrumentation, vol. 6, No. 3, May–Jun. 1972, pp. 230–234.

H. M. Nier, "Automatic Moving Part Measuring Equipment," IBM Technical Disclosure Bulletin, vol. 22, No. 7, Dec. 1979, pp. 2856–2857.

G. J. Brakenhoff et al., "Confocal Scanning Light Microscopy with High Aperture Immersion Lenses," Journal of Microscopy, vol. 117, pt. 2, Nov. 1979, pp. 219–232.

(List continued on next page.)

*Primary Examiner*—Robert P. Limanek
*Assistant Examiner*—David B. Hardy
*Attorney, Agent, or Firm*—Skjerven, Morrill, MacPherson, Franklin & Friel; Alan H. MacPherson

[57] ABSTRACT

A laser imaging system is used to analyze defects on semiconductor wafers that have been detected by patterned wafer defect detecting systems (wafer scanners). The laser imaging system replaces optical microscope review stations now utilized in the semiconductor fab environment to examine detected optical anomalies that may represent wafer defects. In addition to analyzing defects, the laser imaging system can perform a variety of microscopic inspection functions including defect detection and metrology. The laser imaging system uses confocal laser scanning microscopy techniques, and operates under class 1 cleanroom conditions and without exposure of the wafers to operator contamination or airflow. Unlike scanning electron microscopes (SEMs) that have previously been used for defect analysis, the laser imaging system will not damage samples or slow processing, costs significantly less to implement than an SEM, can produce a three dimensional image which provides quantitative dimensional information, and allows sub-surface viewing of defects lying beneath dielectric layers. The laser imaging system is adaptable to cluster or in-situ applications, where examination of defects or structures during on-line processing can be performed.

29 Claims, 6 Drawing Sheets

U.S. PATENT DOCUMENTS

| | | | |
|---|---|---|---|
| 3,187,627 | 6/1965 | Kapany | 88/39 |
| 3,360,659 | 12/1967 | Young | 250/236 |
| 3,497,694 | 2/1970 | Jura et al. | 250/202 |
| 3,602,572 | 8/1971 | Norris | 350/7 |
| 3,705,755 | 12/1972 | Baer | 350/6 |
| 3,719,776 | 3/1973 | Fujiyasu et al. | 178/6.7 R |
| 3,764,512 | 10/1973 | Greenwood et al. | 204/299 |
| 3,775,735 | 11/1973 | Funk et al. | 340/4 R |
| 3,782,823 | 1/1974 | Kantorski et al. | 356/85 |
| 3,790,281 | 2/1974 | Kessler et al. | 356/72 |
| 3,813,140 | 5/1974 | Knockeart | 350/7 |
| 3,926,500 | 12/1975 | Frosch et al. | 350/17 |
| 3,947,628 | 3/1976 | Alien et al. | 178/6.8 |
| 3,980,818 | 9/1976 | Browning | 178/6.6 R |
| 4,045,772 | 8/1977 | Bouton et al. | 340/146.3 B |
| 4,063,226 | 12/1977 | Kozma et al. | 365/125 |
| 4,068,381 | 1/1978 | Ballard et al. | 33/1 R |
| 4,125,828 | 11/1978 | Resnick et al. | 340/146.3 |
| 4,141,032 | 2/1979 | Haeusler | 358/89 |
| 4,160,263 | 7/1979 | Christy et al. | 358/1 |
| 4,194,217 | 3/1980 | van den Bosch | 358/93 |
| 4,198,571 | 4/1980 | Sheppard | 250/571 |
| 4,207,554 | 6/1980 | Resnick et al. | 340/146.3 |
| 4,211,924 | 7/1980 | Müller et al. | 250/311 |
| 4,218,112 | 8/1980 | Ruker | 350/8 |
| 4,223,354 | 9/1980 | Noble et al. | 358/233 |
| 4,236,179 | 11/1980 | Dreyfus et al. | 358/93 |
| 4,255,971 | 3/1981 | Rosencwaig | 73/606 |
| 4,284,897 | 8/1981 | Sawamura et al. | 250/461 B |
| 4,311,358 | 1/1982 | Gibbons et al. | 350/91 |
| 4,314,763 | 2/1982 | Steigmeier et al. | 356/237 |
| 4,343,993 | 8/1982 | Binnig et al. | 250/306 |
| 4,350,892 | 9/1982 | Kay et al. | 250/461.2 |
| 4,354,114 | 10/1982 | Karnaukhov et al. | 250/458.1 |
| 4,366,380 | 12/1982 | Mirkin | 250/306 |
| 4,379,135 | 4/1983 | Sasaki et al. | 436/536 |
| 4,379,231 | 4/1983 | Shii et al. | 250/311 |
| 4,405,237 | 9/1983 | Manuccia et al. | 256/301 |
| 4,406,015 | 9/1983 | Koga | 378/50 |
| 4,406,525 | 9/1983 | Itoh et al. | 350/486 |
| 4,407,008 | 9/1983 | Schmidt et al. | 358/93 |
| 4,455,485 | 6/1984 | Hosaka et al. | |
| 4,485,409 | 11/1984 | Schumacher | 358/294 |
| 4,549,204 | 10/1985 | Bertero et al. | |
| 4,631,581 | 12/1986 | Carlsson | 358/93 |
| 4,636,069 | 1/1987 | Balasubramanian | 356/71 |
| 4,733,063 | 3/1988 | Kimura et al. | 250/201 |
| 4,827,125 | 5/1989 | Goldstein et al. | 250/234 |
| 4,863,226 | 9/1989 | Houpt et al. | 350/6.5 |
| 5,034,613 | 7/1991 | Denk et al. | 250/458.1 |
| 5,035,476 | 7/1991 | Ellis et al. | 350/6.5 |
| 5,046,847 | 9/1991 | Nakata et al. | 356/237 |
| 5,091,652 | 2/1992 | Mathies et al. | 250/458.1 |
| 5,117,466 | 5/1992 | Buican et al. | 382/6 |
| 5,122,653 | 6/1992 | Ohki | 250/216 |
| 5,127,726 | 7/1992 | Moran | 356/237 |
| 5,127,730 | 7/1992 | Brelje et al. | 356/318 |
| 5,153,428 | 10/1992 | Ellis | 250/234 |
| 5,162,641 | 11/1992 | Fountain | 250/201 |

OTHER PUBLICATIONS

C. J. R. Sheppard et al., "Depth of Field in the Scanning Microscope," Optics Letters, vol. 3, No. 3, Sep. 1978, pp. 115–117.

I. J. Cox et al., "Digital Image Processing of Confocal Images," Image And Vision Computing, 1983 Butterworth & Co. (Publishers) Ltd., pp. 52–56.

T. Wilson et al., "Dynamic Focusing in the Confocal Scanning Microscope," Journal of Microscopy, vol. 128, Pt. 2, Nov. 1982, pp. 139–143.

I. J. Cox, "Electronic Image Processing of Scanning Optical Microscope Images," International Conference on Electronic Image Processing, Jul. 26–28, 1982, pp. 101–104.

D. K. Hamilton et al., "Experimental Observations of the Depth–Discrimination Properties of Scanning Microscopes," Optics Letters, Dec. 1981, vol. 6, No. 12, pp. 625–626.

Philip G. Stein, "Image–Analyzing Microscopes," Analytical Chemistry, vol. 42, No. 13, Nov. 1970, pp. 103A–106A.

G. J. Brakenhoff, "Imaging Modes In Confocal Scanning Light Microscopy (CSLM)," Journal of Microscopy, vol. 117, pt. 2, Nov. 1979, pp. 233–242.

W. Jerry Alford et al., "Laser Scanning Microscopy," Proceedings of the IEEE, vol. 70, No. 6, Jun. 1982, pp. 641–651.

H. J. B. Marsman et al., "Mechanical Scan System for Microscopic Applications," Review of Scientific Instruments, vol. 54, Aug. 1983, pp. 1047–1052.

Shura Agadshanyan et al., "Morphoquant—An Automatic Microimage Analyzer of the JENA Optical Works," JENA Review, JR 6, 1977, pp. 270–276.

C. J. R. Sheppard et al., "Optical Microscopy with Extended Depth of Field," Proc. R. Soc. Lond. A, vol. 387, 1983, pp. 171–186.

N. Aslund et al., "PHOIBOS, A Microscope Scanner Designed for Micro–Fluorometric Applications, Using Laser Induced Fluorescence," Physics IV, Royal Institute of Technology, S–100 44 Stockholm 70, (1983 Publication), pp. 338–343.

Eric A. Ash (edited by), *Scanned Image Microscopy*, Academic Press, 1980, pp. 183–225.

P. Davidovits et al., "Scanning Laser Microscope for Biological Investigations," Applied Optics, vol. 10, No. 7, Jul. 1971, pp. 1615–1619.

I. J. Cox et al., "Scanning Optical Microscope Incorporating a Digital Framestore and Microcomputer," 2219 Applied Optics, vol. 22, May 1983, No. 10, pp. 1474–1478.

Paul Davidovits et al., "Scanning Laser Microscope," Nature, vol. 223, Aug. 23, 1969, p. 831.

A. Boyde et al., "Tandem Scanning Reflected Light Microscopy of Internal Features in Whole Bone and Tooth Samples," Journal of Microscopy, vol. 132, Pt. 1, Oct. 1983, pp. 1–7.

Mojmir Petran et al. "Tandem–Scanning Reflected Light Microscope," Journal of the Optical Society of America, vol. 58, No. 5, May 1968, pp. 661–664.

D. K. Hamilton et al., "Three–Dimensional Surface Measurement Using the Confocal Scanning Microscope," Applied Physics B 27, 1982, pp. 211–213.

David A. Agard, "Three–Dimensional Architecture of a Polytene Nucleus," Nature, vol. 302, Apr. 21, 1983, pp. 676–680.

Kenneth R. Castleman, *Digital Image Processing*, 1979 Prentice–Hall, Inc., 1979, pp. 351–359.

IBM Tech. Disclosure Bulletin, vol. 18, No. 12, 1976, p. 1474.

FIG. 3C
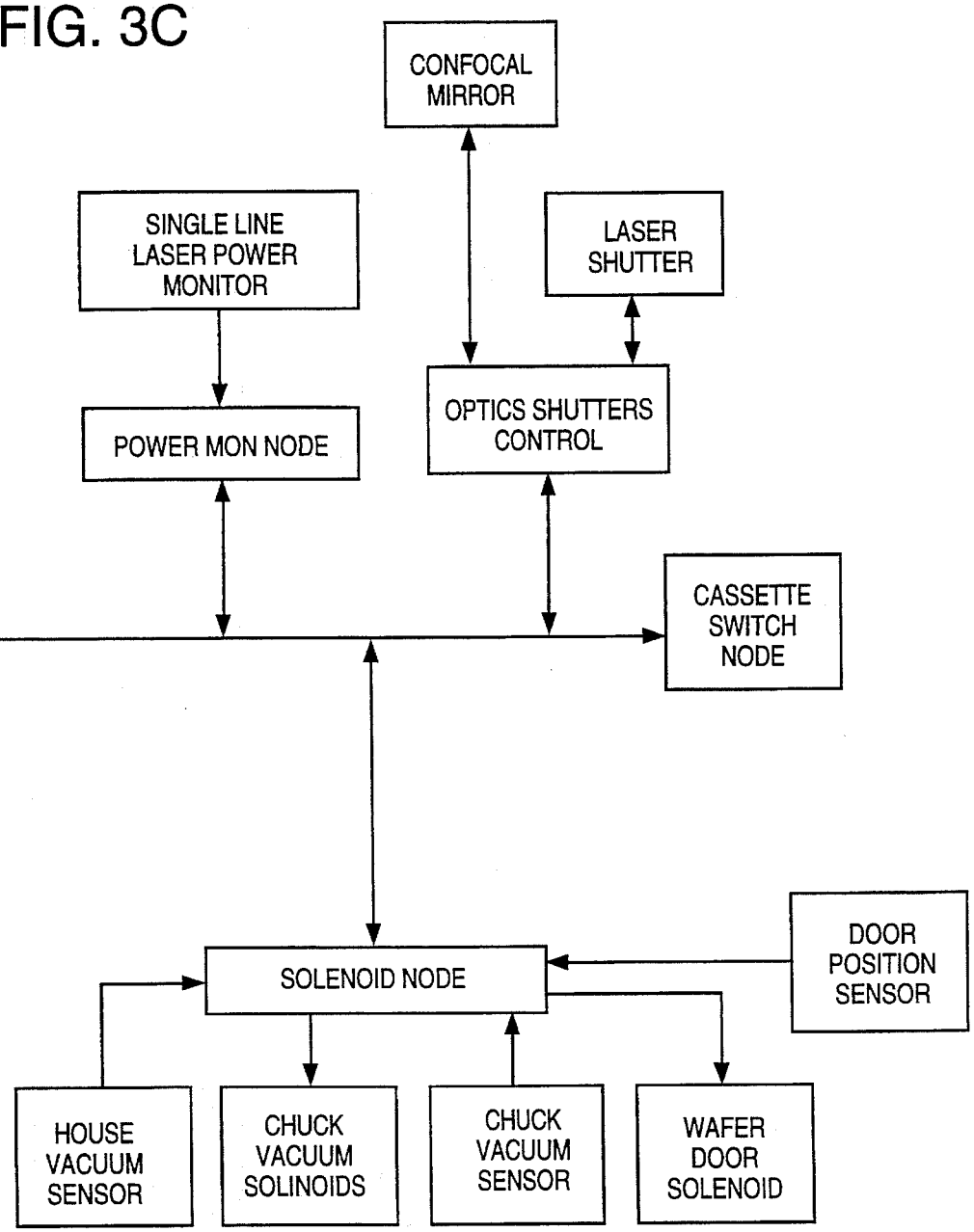
KEY TO FIG. 3
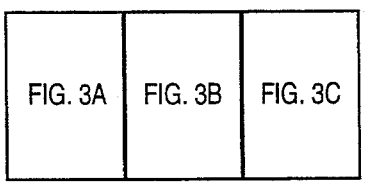
FIG. 3

LASER IMAGING SYSTEM FOR INSPECTION AND ANALYSIS OF SUB-MICRON PARTICLES

CROSS-REFERENCE TO RELATED APPLICATIONS

This application is related to the commonly owned, co-pending U.S. patent application entitled "Surface Extraction from a Three-Dimensional Data Set," by Ken K. Lee, application Ser. No. 08/079,193, filed on the same date as the present application and incorporated by reference herein.

BACKGROUND OF THE INVENTION

1. Field of the Invention

This invention relates to lasers and, in particular, to a laser imaging system for use in analyzing defects on semiconductor wafers.

2. Related Art

Semiconductor chip manufacturers have increasingly sought to improve yields in their production processes. Key to this effort is the reduction of particulate contamination during wafer processing. As the line widths of features on the chip have shrunk from 10 microns several years ago to one micron and below today (with line widths approaching 0.3 micron or less expected in the next few years), the ability to detect and control smaller and smaller particles to achieve higher degrees of cleanliness has become paramount. Additionally, production of acceptable chips requires accurate performance of each of the process steps carried out on the wafer. The value of product on each wafer has also increased dramatically, due to the increasing complexity of semiconductor devices (many more layers and process steps) and the development of larger wafers (up to 200 mm diameter), further accentuating the need for defect detection and control.

Instrument suppliers have addressed a portion of this problem by developing defect detecting systems which scan wafers (wafer scanners) during production for anomalous optical sites that are characteristic of particulate contamination (but may represent other flaws as well). Defects can be either a pit or a bump in the surface of the wafer.

In one type of wafer scanner, in which a laser beam is focussed on and scanned over the surface of the chip (laser scanning system), anomalous optical sites are identified by comparing the light scatter from locations on known good chips to the light scatter from the corresponding locations on the chips being tested. If the two light scatters are different, than an anomalous optical site has been detected. Wafer scanners of this type are made by Tencor Instruments of Mountain View, Calif. as Model 7500, and by Inspex of Billerica, Mass. as Model TPC 8500.

In another type of wafer scanner, a video picture is taken with a conventional video camera of the surface of a known good chip and compared to a corresponding video picture taken of a chip to be tested. Typically, these video systems use white light imaging. The video pictures are analyzed by comparing them on a pixel by pixel basis, i.e., numerical data representing the video image at each pixel is compared and, if the difference falls outside of a pre-established acceptable difference, an anomalous optical site is identified. KLA of San Jose, Calif. makes a wafer scanner of this type as, for example, Model 2131.

The video systems generally cost about three times as much as the laser scanning systems, i.e., the laser scanning systems typically cost approximately $350,000 while the video systems typically cost approximately $1,000,000. However, while the laser scanning systems are more effective in detecting bumps than in detecting pits, the video systems work well in detecting either bumps or pits, and can also sense subsurface defects.

As these wafer scanners were developed, the need to identify positively the nature, e.g., type of material, type of defect (defects are classified broadly as particulate or process flow defects; there are many sub-types within each of these classifications), and the precise location and size of the defects was not appreciated. This information is important for several reasons. Identification of the nature of the defect can be used to determine the origin of the defect. The number, location and size of the defects can be used to calculate the density of defects in general, and, along with identification of the nature of the defects, the density of particular types of defects. This information can then be used to more closely monitor and/or to modify process steps in the chip production process.

As the need for more precise defect analysis has become apparent, semiconductor manufacturers' demand for the ability to "revisit" defects (or a subset of them) found by the above-described wafer scanners, for purposes of positive identification of the nature, location and size of the defects, has led to the hasty design and production of review stations based on laboratory microscopes with precision wafer handling stages that allow an operator to close in on and evaluate the previously detected defects. Revisiting of the defects by the review stations is done off-line from the defect detection process so as not to limit the throughput of the wafer scanners. Little engineering was done in the design of these review stations: in particular with respect to the optics and cleanliness (e.g., the review stations typically use off-the-shelf, visible light, research-style microscopes).

As noted above, the decreasing line widths of features on current and future semiconductor chips increase the importance of detection of contaminants and other defects having a diameter, width, or other characteristic dimension on the order of 0.1 to 0.3 microns. The visible light, off-the-shelf microscopes currently being used in defect review stations lack sufficient resolution to resolve defects of such small size, or to resolve this size structure on larger defects to aid in identification. Visible light scanning microscopes (both white light and laser-based) that are built by modifying off-the-shelf microscopes can improve the resolution significantly, but they are currently in limited use, mostly as part of complex and expensive research setups. Additionally, the use of conventional microscopes increases the risk of contamination of the semiconductor chips during the review process, since a (relatively dirty) human is in close proximity to the wafer surface and because the presence of the microscope causes turbulent flow near the wafer which tends to pull in nearby contaminants to the wafer.

Consequently, the semiconductor processing industry has attempted to use scanning electron microscopes (SEMs) that will provide increased resolution and perform energy dispersive (EDX) analysis. In EDX analysis, X-rays are directed toward the surface of the semiconductor chip. By measuring the wavelength spectrum of the reflected light, information can be gleaned regarding the types of material present on the wafer surface. Unfortunately, EDX analysis requires high voltage (up to approximately 40,000 volts) SEMs; bombardment of the wafer surface with electrons from high voltage SEMs causes damage to the wafer, rendering the wafers unusable for further processing. Recently, low voltage SEMs (100–1000 volts) have seen limited use in wafer fabs for "critical dimension" measurements of line widths, but low voltage SEMs are too slow to use except on a sample basis, and, in addition, provide no analytical (i.e., EDX) capability. Further, in both high and low voltage SEMs, the time to load samples into the SEM and pump down the load-lock chamber containing the SEM is relatively long, undesirably slowing down processing of the wafers. As a result, defect revisiting with SEMs is usually done off-line in a quality control or analysis laboratory.

In an attempt to overcome the limitations of SEMs, some major semiconductor producers have begun to use systems which include both low and high voltage SEMs. However, such systems are expensive, selling in the $1,000,000 to $1,500,000 range.

SUMMARY OF THE INVENTION

According to the invention, a laser imaging system that allows hands-off operation and operates under class 1 cleanroom conditions, has several distinct advantages over conventional systems for sub-micron particle structure evaluation. In one embodiment, the laser imaging system "revisits" defects on production semiconductor wafers, where the defects are first detected (but not analyzed or evaluated) by conventional wafer scanners such as are available from vendors as Inspex, KLA, or Tencor Instruments, among others. The laser imaging system replaces and outperforms conventional microscopes now used to analyze defects on production semiconductor wafers.

Significantly, the laser imaging system according to the invention is the first defect review tool whose optics and functionality have been designed explicitly for efficient performance of the dedicated revisit task. Unlike scanning electron microscopes (SEMs) that have previously been used for defect analysis, the laser imaging system will not damage samples or slow processing, and costs significantly less to implement than an SEM. Further, while SEMs can produce images with resolution on the nanometer scale, they have certain limitations. For example, the SEM image has an extended depth of field, like a photograph taken through a high f-stop aperture, but this image contains no quantitative depth information. Some methods of dealing with this deficiency are sample tilting or coating to produce a "shadowing" effect or perspective change, but these methods require additional process steps and cost, may damage the wafer, and do not completely resolve the problem.

Unlike the SEM, the laser imaging system according to the invention operates in air with class 1 cleanroom compatibility. Also unlike the SEM, the laser imaging system can produce a three dimensional image, using simple image rendering techniques, which provides quantitative dimensional information. The image can be stored and recalled for later viewing. The image can be rotated or tilted or shaded, with correct perspective maintained, without necessity for sample tilting or coating. Additionally, the laser imaging system has an ability the SEM cannot match: sub-surface viewing of defects lying beneath dielectric layers. Combined with three-dimensional analysis software, the user is able to examine cross sections of the defect and surrounding material, and to assess the impact on circuit layers of the wafer.

The laser imaging system presents a real time video image with resolution superior to a conventional microscope. An operator can view the image on a conventional computer display, with comfortable ergonomics, and without exposing the wafers to operator contamination or airflow.

The laser imaging system utilizes confocal laser scanning microscopy techniques, including multiline visible light lasers, and can be optionally fitted with an ultraviolet laser, improving resolution even further due to the shorter wavelengths of the ultraviolet light. The laser imaging system has resolution on the order of 0.1 to 0.2 microns. The laser imaging system can also be used for metrology.

Additional capabilities of the instrument include fluorescence of contaminants (for assistance both in locating them against the complex background of patterned wafers, and in identifying their origins), a variety of software to assist the operator in evaluating and classifying the defect, communications and data storage capabilities for providing trend analysis on-line or off-line, and capacity for image storage.

For future product line expansion, the laser imaging system is adaptable to cluster or in-situ applications, where examination of defects or structures during on-line processing can be performed.

BRIEF DESCRIPTION OF THE DRAWINGS

FIGS. 3A, 3B, and 3C combined are a schematic diagram of the electronics associated with the laser imaging system according to the invention.

DETAILED DESCRIPTION OF EMBODIMENTS OF THE INVENTION

A laser imaging system according to the invention is used to analyze defects on semiconductor wafers that have been detected by patterned wafer defect detecting systems (wafer scanners). The laser imaging system replaces optical microscope review stations now utilized in the semiconductor fab environment to examine detected optical anomalies that may represent wafer defects. In addition to analyzing defects, the laser imaging system can perform a variety of microscopic inspection functions including defect detection and metrology.

Figure 1:
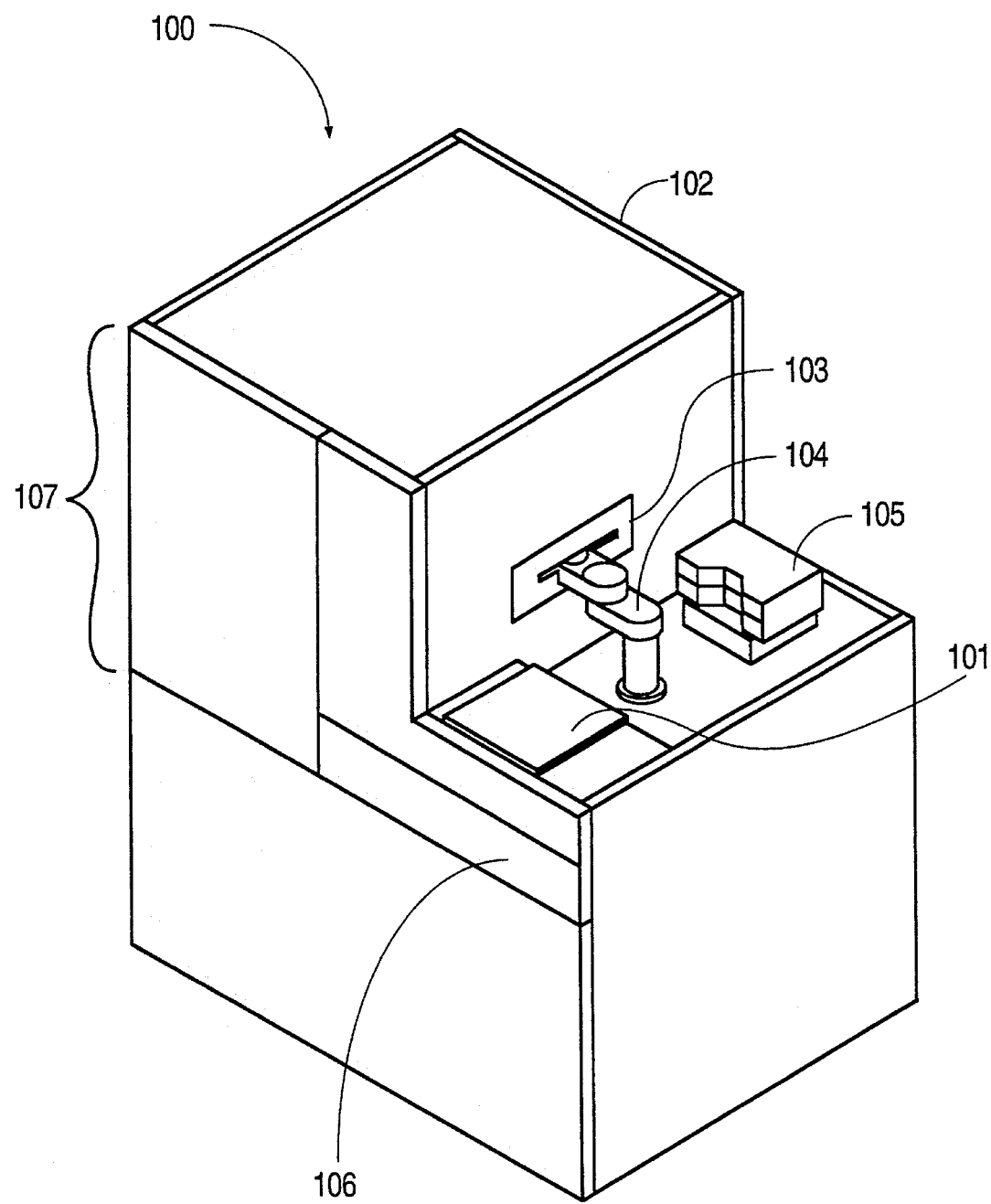
FIG. 1 is a perspective view of a laser imaging system according to the invention.

FIG. 1 is a perspective view of laser imaging system 100 according to the invention. Laser imaging system 100 includes housing 102 made of stainless steel. Laser imaging system 100 occupies a footprint which fits inside a 48" standard clean hood. Laser imaging system 100 has controlled internal airflow (clean air from the cleanroom is drawn in through the top of laser imaging system 100 and exhausted from laser imaging system 100 outside of the cleanroom), maintaining class 1 conditions in the wafer area, which is isolated from the operator console.

A cassette of wafers (not shown) of a given size, e.g., wafers ranging from 3 inches (75 mm) to 8 inches (200 mm) in diameter, is positioned on cassette platform 101. One of a set of interchangeable mounting plates (not shown), there being a different mounting plate for each cassette size (i.e., wafers of different sizes are held by different cassettes), is attached to cassette platform 101. Typically, defects have previously been identified on the wafers by a defect detecting system, as described above. Wafers from the cassette are loaded through wafer door 103 formed in housing 102 into a wafer processing area housed by optics housing section 107 of housing 102. The wafers are either loaded by the operator or by a robot 104 that is part of a standard machine interface (SMIF) i.e., micro-environmentally controlled, interface. The SMIF interface, which is a "box" for transferring wafers in which clean room conditions are maintained, is conventional and is available from Asyst Technologies in Milpitas, Calif. (various models are available and can be used with the invention). After inspection, the wafers are unloaded by either the operator or the robot 104. An optional 3-cassette carousel (not shown) may be mounted on laser imaging system 100 allowing sorting of wafers after inspection.

Robot 104 is a conventional precision, high reliability (less than one wafer drop per million transfers) robotic wafer handler, such as is available from MECS in Japan as part no. UTX-1000. Robot 104 will reliably sense, load, and unload wafers from cassettes, interchangeably handling 75 mm to 200 mm wafers. Robot 104 senses missing or skewed wafers in the cassette(s), as well as the presence or absence of a wafer on the robot arm or vacuum chuck 224 (see FIG. 2). Robot 104 (and other components of laser imaging system 100) is designed to eliminate any wafer contamination (laser imaging system 100 maintains Class 1 compatible cleanliness while handling wafers). Robot 104 has sufficient utility backup (power, air, vacuum) to protect any wafer in transit on robot 104 from damage. Upon restart after a power failure, all wafer locations (cassette slots, robot arms, vacuum chuck 224 (FIG. 2), plus missing cassettes, are sampled for the presence or absence of wafers and/or cassettes, and appropriate responses made.

When loading wafers, robot 104 removes wafers from cassette platform 101 and performs a pre-alignment step, using pre-aligner 105 which senses a notch and/or flat(s) on the wafer. Optionally, any bar code (identifying the particular wafer) which may be present on the wafer may also be read at this time.

While the wafer is being loaded, a file of data from the defect detecting system, specifying the wafer coordinates of the detected defects, is transferred to the laser imaging system computer within housing 102 (not visible in FIG. 1), either by diskette or other media, or by communication via a link or network such as Ethernet, RS232, etc. A computer for use with laser imaging system 100 is available from Silicon Graphics in Mountain View, Calif. as part no. SGI XS24Z. A disk drive, available from Silicon Graphics in Mountain View, Calif. as part no. P3-F252, and tape drive, available from Hamilton/Avnet in Mountain View, Calif. as Maynard (Archive) 21501S, are attached within disk drive bay 106 of housing 102.

Figure 2:
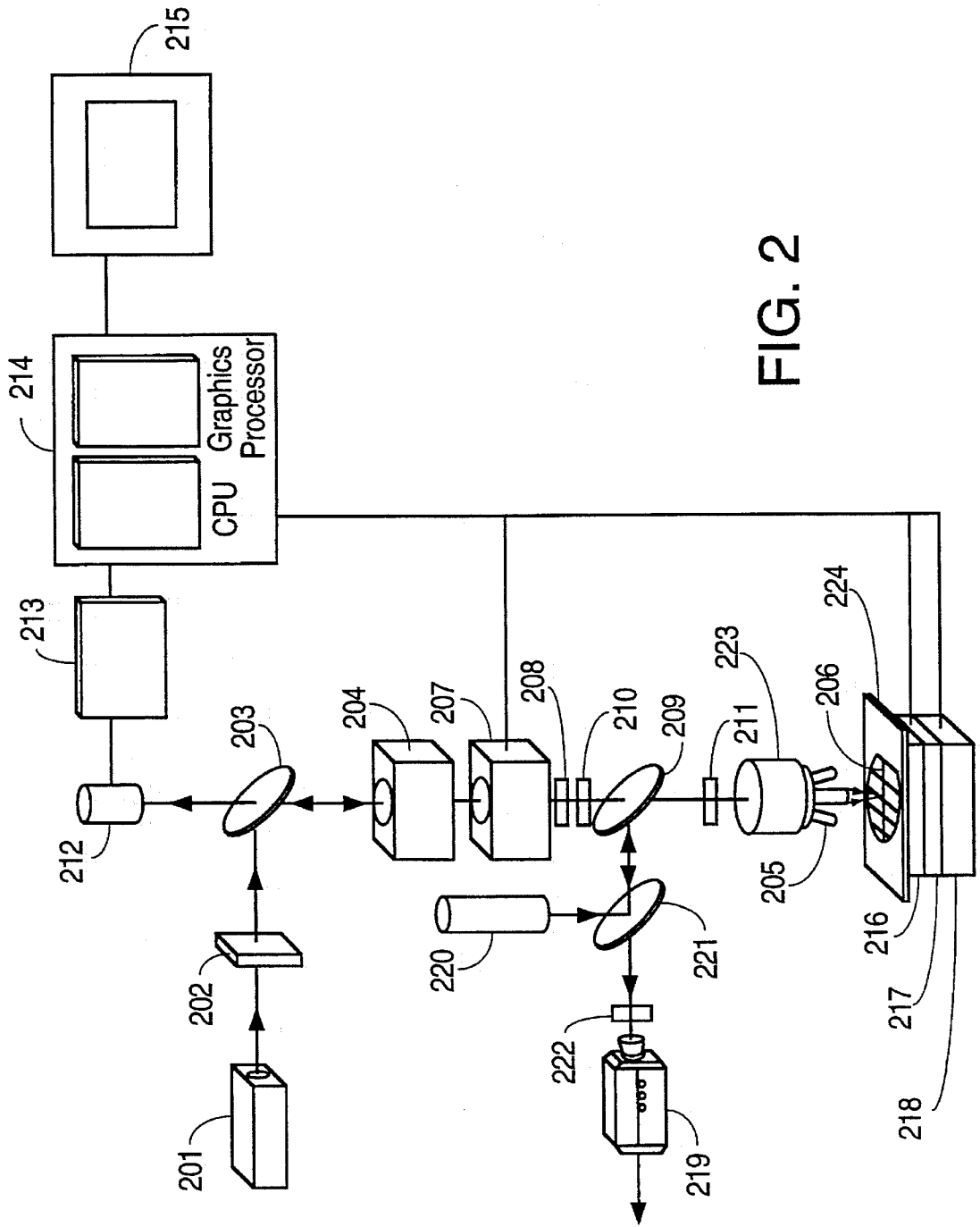
FIG. 2 is a schematic diagram of a laser imaging system according to the invention illustrating the operation of the laser imaging system.

After pre-alignment, the wafer is loaded into the wafer processing area through wafer door 103 onto the optical unit's XYZ-stage (translational motion) and is secured on a conventional vacuum chuck 224 (FIG. 2). (In this description, a Cartesian coordinate system is used in description of various aspects of the system. The X and Y axes define a plane parallel to the patterned surface of the wafer and the Z-axis is perpendicular to the patterned surface of the wafer.) The system translates the wafer to the first "de-skew" point (i.e., pre-determined orientation of the wafer that accounts for the mis-orientation of the patterns on the wafer with respect to the wafer flat and the robot 104 placement error), and automatically focuses using the laser as described below. The operator accomplishes fine alignment of the wafer (de-skew point) by lining up the visible light microscope field of view with etched fiducial marks or other pre-specified structures on the wafer surface. After this precise de-skew alignment, the system can accurately translate any specified location on the wafer into the field of view of the microscope with an accuracy of a few microns.

The heart of laser imaging system 100 is the laser scanning microscopic optics module ("optics head") which includes elements 201, 202, 203, 204, 205, 207, 208, 210, 211, 212, 219, 220, 221, 222, and 223 shown in FIG. 2 below. The optics head includes a laser, confocal beam-scanning optics, and ultraviolet and visible photo detection electronics, together with commercial microscope components to achieve high quality real time confocal images. Laser imaging system 100 will produce a complete XY-scanned laser image, in a single plane of focus, at video rates. The resulting image is displayed on a high resolution monitor, also in real time. Thus, the operator can scan through different levels of focus in real time, as with a conventional microscope.

FIG. 2 is a schematic diagram of laser imaging system 100 according to the invention illustrating the operation of laser imaging system 100. Laser imaging system 100 uses the basic principles of confocal microscopy, in which illuminating light passes through a pinhole, and the image of this pinhole is then cast by the system optics on the sample to be viewed. The light scattering from the sample returns through the system optics to the pinhole, but only light from the focal plane of the imaging (objective) lens returns through the pinhole, i.e., light from the plane through the sample at which it is desired to obtain imaging data.

Laser imaging system 100 includes an air cooled, multi-line argon ion laser 201 which provides up to six different wavelengths of light for imaging surfaces and structures in semiconductors. An example of a laser that can be used with the invention is the Model 2204-25ML air-cooled argon ion laser produced by Uniphase Corporation, San Jose, Calif. It is important to perform imaging with a selection of wavelengths of laser light to overcome absorption, reflection, and interference problems that can occur for a specific wavelength for a given material. That is, one wavelength will not give good results for all materials, film thicknesses, and surface properties. Additionally, in many cases, it is desirable to observe through one or more top layers of material (typically dielectric) which will reflect or absorb some wavelengths strongly, but will allow transmission of others to perform the imaging desired. Other wavelength lasers (such as Helium-Neon or Helium Cadmium) could also be used to supply light at other wavelengths.

Laser 201 produces polarized light at several discrete wavelengths. The light passes through a "notch" filter 202 mounted on a conventional computer controlled filter wheel (not shown) within optics housing section 107. Notch filter 202 isolates a laser line or lines. A notch filter for use with the invention is available from Edmund Scientific of Barrington, N.J. as part no. 43120. Other filters are available from the same source for other wavelengths.

The light having the selected wavelength(s) passes from notch filter 202 to polarizing beam splitter 203. Polarizing beam splitter 203 is attached to selectable notch filter 202 using conventional optical mounts. Polarizing beam splitter 203 preferentially reflects light only of the proper polarization and directs the light to spatial filter 204. The polarization of the light emitted from laser 201 is oriented so that most of the light is reflected by polarizing beam splitter 203 at 90 degrees into the focusing optics of spatial filter 204. A small portion of the light passes through polarizing beam splitter 203 to a conventional power monitor diode (not shown) mounted behind polarizing beam splitter 203, where the light is absorbed. A polarizing beam splitter for use with the invention is available from Melles Griot of Irvine, Calif. as part no. 03PBB003.

Spatial filter 204 consists of optics which expand the beam and then focus it on a pinhole aperture. The diameter of the pinhole aperture is selected according to well-known techniques to re-image the light through the downstream optics and a selected one of a plurality of objective lenses 205 to produce a diffraction-limited spot on wafer 206. The diameter of the pinhole aperture is also selected to allow easy alignment of the beam of light and a significant amount of high power light to pass through the aperture. A spatial filter for use with the invention is available from Melles Griot of Irvine, Calif. as Compact Spatial Filter Newport/ 910. Spatial filter 204 is attached to polarizing beam splitter 203 by conventional optics mounts.

Subsequent optics within spatial filter 204 and between the pinhole assembly and the scanner mirrors collimate the light, and direct the light to mirrors mounted on X-Y beam scanner 207. An X-Y beam scanner for use with the invention is available from General Scanning of Watertown, Mass. as part no. 000-3011003. X-Y beam scanner 207 is attached to spatial filter 204 by conventional optics mounts. The mirrors in X-Y beam scanner 207 can oscillate their angle with respect to the beam of light passing through X-Y beam scanner 207. X-Y beam scanner 207 includes two oscillating galvanometers, one a high speed resonant unit operating at 8 kHz, the other a servo controlled unit, operating at 13 or 26 Hz (but capable of other speeds). The servo steps in small increments, so that the X-Y beam scanner 207 traces out a raster pattern in space. A raster scan of 256 or 512 lines is produced at approximately 26 or 13 frames per second, and is imaged at the back focal plane of the tube lens 211.

This raster pattern is imaged in space by the scan lens 208 in the plane of the field lens (not shown, but between beam splitter 209 and quarter wave plate 210). A scan lens for use with the invention is available from Applied Optics of Pleasanton, Calif. as part no. 000424. Scan lens 208 is attached to X-Y beam scanner 207 by conventional optical mounts. The field lens serves to collect high angle light, providing a more uniform brightness across the raster pattern and allowing more light to reach the tube lens 211, described below, without distorting the image. The tube lens 211 and objective lenses 205, described in more detail below, are standard infinity corrected optics.

Quarter wave plate 210 is attached to scan lens 208 and is positioned to convert the linearly polarized laser light to circularly polarized laser light. A quarter wave plate for use with the invention is available from Melles Griot of Irvine, Calif. as part no. 02WRM005. Beam splitter 209 is attached to quarter wave plate 210 by a conventional optical mount, and is explained in more detail below. Tube lens 211 is attached to beam splitter 209 by a conventional optical mount and works with objective lens 205 to de-magnify the raster scanned pinhole image and project it on the wafer 206. A tube lens for use with the invention is available from Olympus of Japan as part of their vertical illuminator model SLM220.

The image of the light spot is focused and demagnified by the objective lens 205 in the focal plane of the objective lens 205. Objective lenses 205 for use with the invention are available from Olympus of Japan by specifying 100xBF 1-LM590. Many interchangeable lenses are available. Objective lenses 205 are mounted on a computer controlled motorized turret 223 that enables automatic changing of objective lenses 205 and autofocus (one lens is focused and focus offsets stored in the computer are used to automatically focus the other lenses) of each objective lens 205. A turret for use with the invention is available from Olympus of Japan as part no. BL0920. Turret 223 is designed to accommodate three to six objective lenses 205, and can handle low power (magnifications of 5, 10 and 20 times actual size) as well as medium power (magnification of 50 times actual size) and high power, high N.A. (numerical aperture, a conventional designation for the light gathering property of an objective lens in which higher numbers indicate a broader cone of gathered light) objective lenses 205 (magnifications of 100 and 150 times actual size and 0.95 N.A.). Turret 223 and a vertical illuminator containing tube lens 211 as a standard component are mounted together with a flange and held by a locking screw. The turret/ illuminator assembly bolts to the optics baseplate.

According to the principles of confocal imaging, the light striking wafer 206 is scattered and a portion of the light reflected back into objective lens 205, returning through the optical path described above. As the returning light passes through quarter wave plate 210, the returning light is converted to light linearly polarized and 90° out of phase with respect to the polarization of the light originally emitted by laser 201. The light continues back along the path through the field lens, scan lens 208, and mirrors of X-Y scanner 207 until the light reaches the pinhole aperture of spatial filter 204. If the light spot was in focus on the sample, the image is imposed on the aperture. If the light spot was out of focus on the sample, very little light returns through the aperture. Consequently, signals in the confocal optics get darker, not merely blurred, as occurs with conventional optics, when the sample is out of focus. Light which passes through the aperture reaches the polarizing beam splitter 203, which, being oppositely polarized, passes through polarizing beam splitter 203 undeviated and is imaged on the photodetector 212.

By measuring the light intensity at each XY location of the raster scan, a map of light intensity in the focal plane of the objective lens 205 is constructed. This map can either be stored in the memory of system computer 214, or analyzed by surface data processor 213, which stores the readings, and makes a comparison of the intensity with previously stored maps from other scans, as described below. The light intensity map is also written directly into the video memory of the system computer 214 and may be displayed live on the computer display 215 in an appropriate window, as described below.

To obtain a three dimensional image, the optics head works with the fine z-stage control 216 to develop an expanded depth-of-field image. The sample height is stepped over a pre-selected vertical interval (typically 12 nm or some multiple thereof) using the fine z-stage control 216. After each complete raster scan at a particular sample height, the height of the sample is changed using fine z-stage control 216, and a new raster scan performed, as described above, to obtain a map of light intensity in the focal plane of objective lens 205 (at the new sample height) by measuring the light intensity at each XY location of the raster scan.

X-Y stage control 218 is used to position the defect or region of interest in the field of view. The X-Y stage control is then held still while the fine z-stage control 216 is used as described above.

A three-dimensional image can be obtained from the multiple XY light intensity maps in one of two ways. First, as noted above, the XY data from each raster scan can be analyzed by surface data processor 213 by comparing the light intensity at each point of the XY scan with corresponding points of a "master map." This "master map" stores the maximum light intensity values found at each XY point, these values resulting from previous comparisons of XY light intensity maps. The Z-axis location of the maximum light intensity at each XY location is also stored. After all of the XY light intensity maps have been obtained and compared to the "master map," the data representing the light intensity maximum at each XY location and the Z-axis location of each light intensity maximum are used to construct the three-dimensional image of the wafer surface. With this method, it takes about 5 seconds to acquire all of the light intensity data and extract the surface.

Alternatively, especially if the wafer is multilayered, i.e., producing multiple peaks at each XY location along the Z-axis (which might occur, for instance, where transparent layers are formed), each light intensity map can be stored in system computer 214, along with the Z-axis height of each map. If it is desired to create a three-dimensional image of the surface of the wafer, the XY light intensity maps are successively compared to determine the maximum light intensity at each XY location. The Z-axis location of the maximum light intensity at each XY location is stored and, at the conclusion of the series of comparisons of the XY light intensity maps, is used with the maximum light intensity data to construct the three-dimensional image of the wafer surface. With this method, it takes about 35 seconds to acquire all of the light intensity data, then extract the surface using a processor in system computer 214.

A process for constructing a three-dimensional image of a surface from a three-dimensional data set is described in more detail in commonly owned, co-pending U.S. patent application entitled "Surface Extraction from a Three-Dimensional Data Set," by Ken K. Lee, application Ser. No. 08/079,193, filed on the same date as the present application, the pertinent disclosure of which is hereby incorporated by reference.

The raster scan is repeated 13 times per second for a 512 by 512 pixel image, or faster for smaller (i.e., fewer pixels such as 256 by 256) images. (Note that raster scan sizes other than 512 by 512 or 256 by 256 can be used.) A complete three-dimensional volume data set will typically include 64 raster scans (other numbers can be used), for a total data array of size 512 by 512 by 64. For a 512 by 512 pixel image, the total time to accumulate the data to construct the three-dimensional image of the surface (assuming 64 raster scans, i.e., vertical height steps) is approximately five seconds.

The light intensity at each data point is stored in system computer 214 as an 8-bit quantity. A simple map of a three-dimensional surface is created using the three-dimensional graphics (such as the Silicon Graphics Inc. Graphics Library, available as part of the XS24Z computer package) of system computer 214 by plotting the X, Y, and Z position of each maximum intensity point, and displaying the map as a continuous surface. The brightness of each point on the surface is determined by the light intensity measured at that point. The map display may be done in gray scale, in false color converted from the gray scale, in a mode showing shape (position) only, or shape with height represented in gray scale.

The capacity for white light imaging, in addition to the laser imaging described above, is another feature of laser imaging system 100. As noted above, beam splitter 209 is attached between quarter wave plate 210 and tube lens 211. By imposing beam splitter 209 in the path of light from laser 201 just prior to tube lens 211, and using suitable filtering that blocks the reflected laser light but lets other wavelengths pass to the video camera, a conventional microscope image can be obtained, in addition to the laser image, by using a conventional microscope illuminator 220 and video camera 219, charge coupled device (CCD). The white light imaging is accomplished without the use of microscope eyepieces that would result in undesirable proximity of the operator to the wafer being analyzed that may result in contamination of the wafer. Rather, the microscope image is displayed on a computer display (simultaneously with the laser image, if desired), either in a separate window on computer display 215, using software described in more detail below, or on a separate video monitor display (not shown).

The white light microscope image is produced alone or simultaneously with the live laser image by video camera 219 available from COHV of Danville, Calif. as part no. 8215-1000 which views the sample in white light emitted by microscope illuminator 220, and inserted into the optical path by beam splitter 221. A microscope illuminator for use with the invention is available from Olympus of Japan as part no. 5LM220. A beam splitter for use with the invention is available from Melles Griot of Irvine, Calif. as part no. 03BSC007. Filter 222 blocks the laser line in use, but passes broad bands of light having other wavelengths, so that laser light from laser 201 is prevented from saturating the image at video camera 219 with reflected light. A filter for use with the invention is available from Edmund Scientific of Barrington, N.J. as part no. 22754. Video camera 219 and filter wheel 222 are mounted on brackets which position video camera 219 and filter 222 in line with beam splitter 221. Beam splitter 221 is mounted on the turret assembly with conventional optical mounts.

To get a white light image alone, laser imaging system 100 can remove beam-splitter 221 and substitute a mirror (not shown) so that only the video camera light path is active. Then, the blocking filter (mounted on a filter wheel) can be removed and the full spectrum white light image viewed.

Figure 3A:
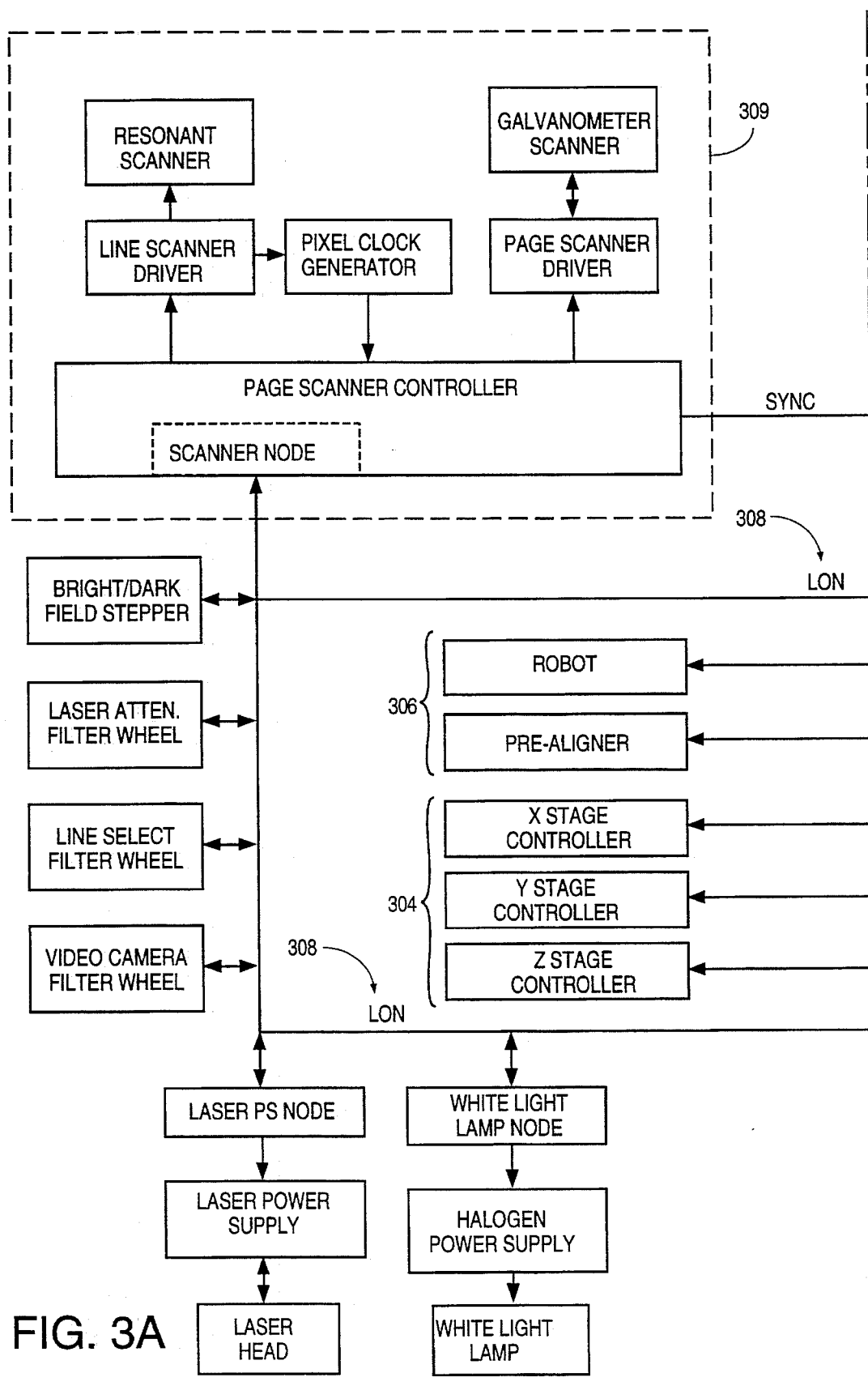
Figure 3B:
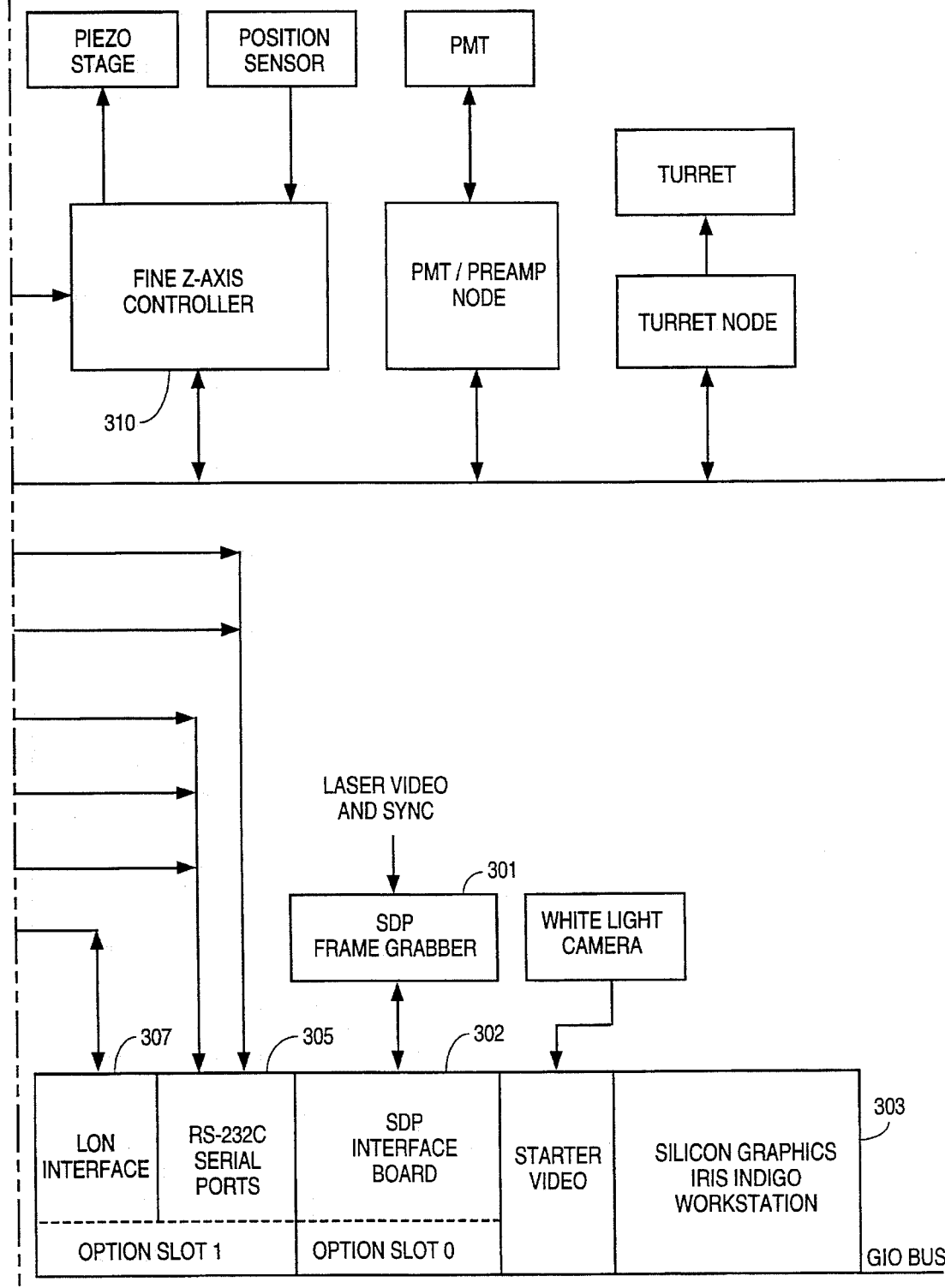

FIGS. 3A, 3B, and 3C combined are a schematic diagram of the electronics associated with laser imaging system 100. FIGS. 3A, 3B and 3C show all analog and digital electronics, plus power supplies, for complete operation of laser imaging system 100. Laser imaging system 100 operates on 220 volts (200–240 volt nominal), 50/60 Hz single phase electric power (or the European and Japanese equivalents).

The SDP Frame Grabber 301 interfaces with photo detector 212 (FIG. 2) and is synchronized with the scanner electronics 309, and fine z-stage control 310, to digitize the photodetector data and produce a three-dimensional map of light intensity which can either be stored directly in the computer memory, or processed to immediately extract a surface image. The SDP Frame Grabber 301 interfaces through the SDP interface 302 to the system computer 303 (also shown as 214 in FIG. 2). SDP Frame Grabber 301 is fast and enables surface data to be extracted from the volume data.

The system computer 303 is a high speed RISC graphical workstation, such as a Silicon Graphics Iris Indigo XS24Z manufactured by Silicon Graphics of Mountain View, Calif., or equivalent, capable of handling concurrent tasks of robot functions, stage motion, operator interface, and optics control, while also performing image processing functions. In addition, system computer 303 must work with a windowing user interface and high resolution color graphics.

The X, Y, and coarse Z stage controllers 304 communicate with system computer 303 via an RS-232C interface 305, as do the robot and pre-aligner controllers 306.

The balance of the system electronic functions communicate through Local Operating Network (LON) interface 307 built on the same interface slot as RS-232C interface 305. The LON 308 itself is a pair of wires that plug into each node serially around the system. Each node contains a local processor and firmware for LON communications, self diagnosis, and local operation of certain functions.

All user interface is via an operator console that is part of system computer 303 and which includes computer display 215, a mouse/trackball, a joystick controller, and a keyboard. The operator console may optionally be remotely mounted (i.e., outside the cleanroom). Image processing and analysis functions may be controlled from the console. Through these controls and the windowing software, the operator can set up, program and operate any part of laser imaging system 100 including wafer selection and handling, defect editing and selection, automatic and/or manual wafer loading, defect classification, etc. For example, the joystick controller allows the user to move the coarse Z-stage control 217 in small increments, to bring an object or region of interest on the wafer into view. Alternatively, for enhanced ease in making very small lateral movements, the operator can use the mouse to point and click to cause the X-Y stage control 218 to change position.

The operator has three modes from which to select viewing: white-light conventional microscope optics ("white light mode"), real time laser scanning optics ("laser mode"), or both laser and white light optics simultaneously ("combination mode"). In white light mode, the operator can select from one of several objective lenses, varying effective magnification of the image. (The laser image scales simultaneously with the white-light image.)

Laser or white light imaging of a region of the wafer produces data regarding the wafer characteristics in the imaged region. The data is stored on system computer 214. After imaging of a region of the wafer, the operator examines each defect image as laser imaging system 100 presents it to him. If the defect is not in view (if, for instance, the defect location data from the wafer scanner is slightly erroneous), or the operator wishes to examine a larger or different area, the joystick controller allows him to "cruise" the wafer. After the operator examines the defect, the operator classifies the defect, optionally records the image, and proceeds to examine the next defect. Upon completion of review of all desired defects, or other inspection tasks, the wafer is returned to its cassette, and the next wafer loaded, repeating the process above.

In the live laser image, presented in a particular window of the screen of computer display 215, as explained in more detail below, the operator sees a real-time narrow depth of field laser image, which may be zoomed to higher effective magnifications. The operator can translate the sample in the Z-direction (vertical direction) to cover an entire vertical region of interest. The operator can also select a range of vertical motion, and have laser imaging system 100 construct a 3-dimensional image of the region specified. Automatic ranging (automatic selection of vertical distance to traverse in obtaining imaging data), automatic focus (automatic focusing of objective lens at desired vertical location) and automatic gain control (automatic adjustment of the photodetector gain to compensate for differences in the reflectivity of the wafer) may also be employed to automate most of the operator's tasks in acquiring the three-dimensional image. The three-dimensional image may be examined in pseudocolor, profiled, shadowed, rotated, etc.

The user can utilize laser imaging system 100 as a white light microscope. The microscope view is presented in a different window than the laser view. In white light mode, the user can select views (e.g., two-dimensional), translate (X-Y movement) and focus on details (Z-direction movement), change objective lens magnification.

The overall system software is designed for operation of laser imaging system 100 in both operator and engineering mode, optionally using defect files supplied by various wafer scanners in a variety of formats. Both operator and engineering mode are password protected separately, as explained in more detail below.

In engineering mode, the user can use a recipe development editor to develop recipes for routine inspection of specified types of wafers at specific process steps for that wafer, i.e., to pre-specify operating parameters for use by operators working on a specific process level and product. The recipes can specify which screen and windows are to be used, enable the laser wavelength and power to be used to be selected, specification of the number of slices of data and their spacing (in nanometers), autofocus to be specified, and the offset in the z-direction (vertical direction) from the autofocus position to the ideal viewing position to be preset.

Engineering mode also allows access to system maintenance functions such as utilizing the LON access to run diagnostic checks on the electronics or recalibrate XY and Z stage motion In operator mode, the operator loads, inspects and classifies lots of wafers per the predetermined recipe associated with the particular lot number and wafer ID. The operator has limited options to alter the inspection sequence.

Utilities are available in pop-up menus to enable manual control of the fine Z-stage control 216, coarse Z-stage control 217 and X-Y stage control 218, polling of stage variables, and robot manual control (e.g., to allow movement of a wafer from the flat finder or stage after a power failure). Diagnostics can also be called up via a pop-up window displaying all LON nodes and system variables. The status of LON nodes can be checked and revised. From the display of LON nodes, direct control of system functions, e.g., open and close the laser shutter, can be accomplished.

As an aid to workers reviewing defects (especially during production), laser imaging system 100 has the capability to store wafer images and to bring them up in Library windows. These images are usually stored as bit maps and can be used to represent typical defects for comparison by the operator with the defect currently being classified. Laser imaging system 100 can be configured to bring up such images automatically as different defect classifications are selected. Bit map images from other devices, such as white light microscopes or SEMs can also be stored and recalled, for comparison between inspection systems, thus enabling the operator to compare the image produced by laser imaging system 100 with familiar images. The bit maps can be displayed in special windows to help operators classify defects.

The system software includes different levels of password protection. At one level, engineering personnel can access laser imaging system 100 to set up predetermined recipes for screen configuration, laser scan parameters, and defect codes. At a different level, operators can access laser imaging system 100 to call up the recipe for the particular wafer level and product being used in order to examine defects on wafers to be inspected. This feature, combined with automatic focus, ranging, and gain control, allows competent operation of laser imaging system 100 with a minimum of operator training.

Laser imaging system 100 uses an Ethernet interface that supports standard file transfer and management (data and recipe upload/download, etc.). Laser imaging system 100 includes software for generating output report files for use by data analysis (trending, statistical analysis, etc.) software as well as printed reports. A number of confocal images may be stored in files for subsequent review on or off line from laser imaging system 100.

As noted above, laser imaging system 100 includes computer display 215. Computer display 215 displays pictorial and numerical results of the analysis of the defects on the semiconductor chips, and lists menu selections for control of laser imaging system 100. Laser imaging system 100 provides the capacity for displaying any number of different display screens on computer display 215. Each display screen is defined by the number, type, size and location of the windows included within the display screen. The number of windows that can be displayed on a display screen is limited only by the size of the windows to be displayed. Generally, the types of windows that can be displayed on each screen are icon windows, picture windows and information windows.

Figure 4:
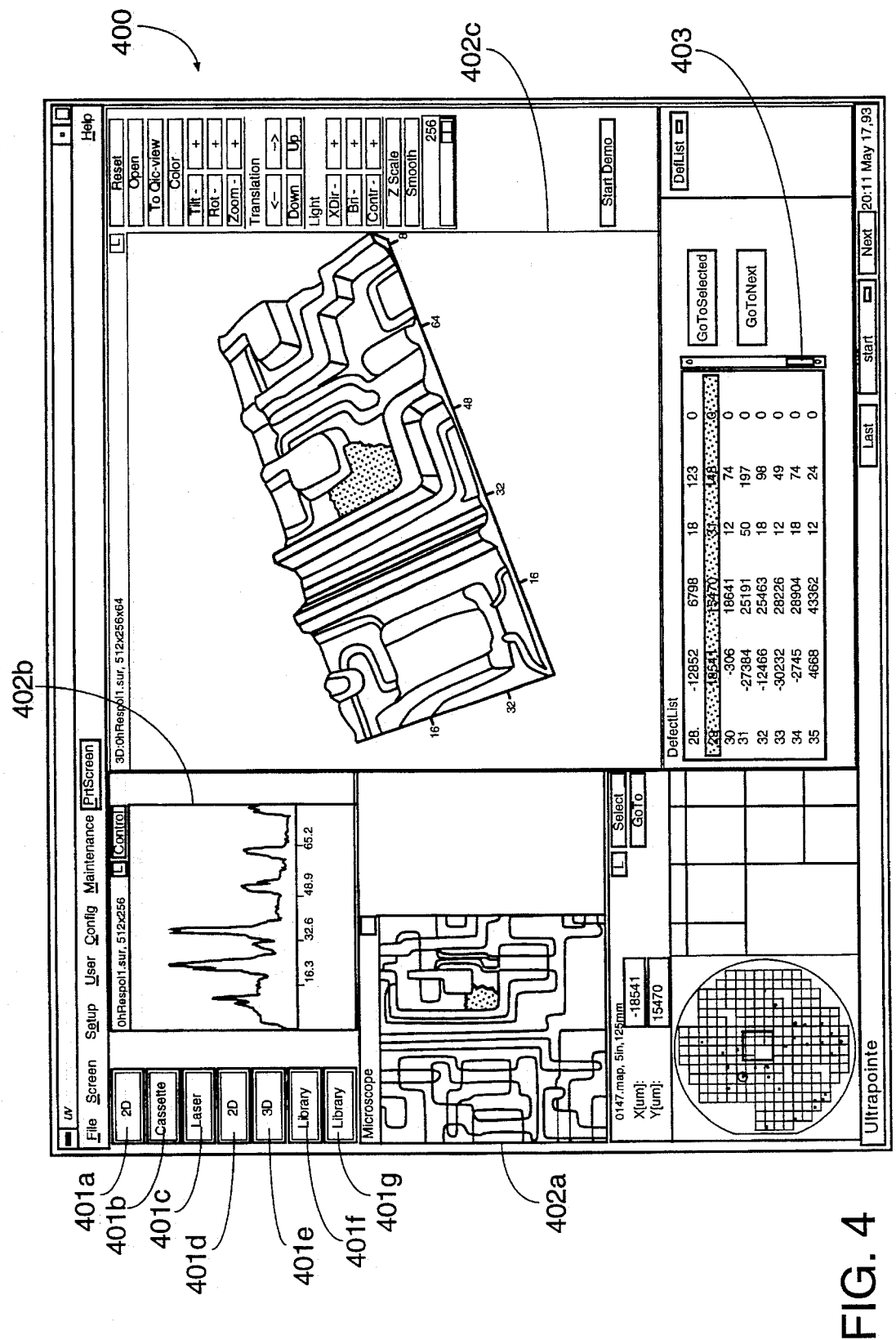
FIG. 4 is a view of a display screen resulting from analysis of an area of the surface of a semiconductor chip by a laser imaging system according to the invention.

FIG. 4 is a view of display screen 400 resulting from analysis of an area of the surface of a semiconductor chip by laser imaging system 100. Display screen 400 includes a plurality of windows of various types. In FIG. 4, windows 401a, 401b, 401c, 401d, 401e, 401f and 401g are icon windows; windows 402a, 402b, 402c are picture windows; and window 403 is an information window.

In FIG. 4, the icon windows list choices for pictorial display in the picture windows. For instance, icon windows 401a and 401d command display of a two-dimensional image in one of the pictorial windows, e.g., the surface profile seen in window 402b or the planar surface view seen in FIG. 402a. Icon window 401e commands display of a three-dimensional image in one of the pictorial windows, e.g., the three-dimensional surface image seen in window 402c. The pictorial windows 402a, 402b and 402c show two or three-dimensional images of the semiconductor chip being analyzed, as discussed above. The information window 403 gives tabular information regarding the size and location of particular defects on the chip and is describe in more detail below.

Laser imaging system 100 includes a number of pre-defined screens (in one embodiment, on the order of 4–5 screens), i.e., screens having windows of a pre-determined type and size located at pre-determined locations. However, laser imaging system 100 includes the capability for a user to define an unlimited number of screens, each screen having any desired combination of windows according to window type, window size and window location.

The screen (window and arrangement of windows) to be displayed is selected by the operator. For each screen, each pictorial window is stored as an icon window when not in use. Windows in different regions of the screen may be interchanged by "clicking and dragging" the window to the new location.

The Microscope Window contains a live video presentation of the white-light image taken from the wafer surface through the microscope objective lens. This image may be viewed simultaneously with the laser image or can be view in white-light only mode for optimum viewing of the white-light image.

The Laser Window directly displays the live laser image produced by the scanning laser beam. Controls for changing the focus of the laser through its range are available. Additional controls include autofocus, laser intensity, zoom, number of slices to utilize for a three-dimensional image, and the step size of three-dimensional image slices, plus other imaging control features.

The 2-D Window utilizes the acquired three-dimensional surface image, and presents a two-dimensional image of a slice through the three-dimensional data. In "XY" mode, the 2-D Window displays a top view in false color of the wafer surface, i.e., a projection of an effectively infinite depth of field image of the wafer surface. In "XZ" and "YZ" modes, the surface image is represented as surface profiles of selected vertical slices. In the two-dimensional images, a rubber band metrology box (i.e., a variable size cursor box) can be used to determine the size (in the plane chosen) of the defect. In "cut" mode, the "XY" mode view includes cursor lines which can be controlled by, for instance, a mouse to select "XZ" mode or "YZ" mode slices. If the 2-D Window is used with a volume data set rather than a surface data set, the "XY" mode display shows a single slice scan of data, rather than a surface outline. The "XZ" mode and "YZ" mode show vertical cuts through the data set. Special options allow profiles of volume data sets to show multiple layer structures. This occurs by analyzing volume data from multilayer semi-transparent samples.

The 3-D Window projects a perspective view of the surface image. The 3-D Window may be rotated, tilted, zoomed, shaded, etc. by the operator to obtain a desired image for analysis.

The Wafer Map Window displays the defect map of the wafer under inspection, the defect map having been produced by a wafer scanner that is not part of laser imaging system 100. Defects are shown as a color-to-size coded dot on the screen. The operator can select a defect to revisit by, for instance, using a mouse to "point and click" on the defect. A rubber band metrology box may be used to display a portion of the defect map to higher precision in an enlarged view. Alternatively, a list of defects can be brought up in a pop-up text window (the defect locations are given as coordinates of a Cartesian coordinate system), scrolled through and selected directly by highlighting items on the list.

The Cassette Map Window diagrammatically represents a loaded cassette. The operator can select and load any wafer from the cassette by, for instance, using a mouse to "point and click" on the wafer. The operator can also unload the wafer to a cassette on the cassette platform 101 of laser imaging system 100.

There is a major advantage to using a laser with multiple lines to image surfaces, to account for different reflectivities and absorption. It is always a problem to focus microscopes automatically. Confocal optics are a natural way to perform an autofocus due to the extremely narrow depth of field. However, a single spot autofocus may not work well if a very dark spot on the sample is being imaged. By scanning the laser spot in real-time, and averaging over the return signal, a much more reliable autofocus is obtained. If a particular material is strongly absorbing, different wavelengths may be selected. Alternatively, a laser filter may be used which transmits each wavelength of the laser inversely proportionally to the intensity of the wavelength and so illuminates the sample with multiline laser light which is sure to select at least one wavelength which reflects strongly. In a simpler mode, the laser can be used with no filter, and the computer can adjust laser power and photodetector gain to achieve a good autofocus.

False color can be used to see small defects, either on the surface or under the surface. By converting images to false color from black and white, very small objects may be detected that would otherwise go unnoticed, because the human eye can discern thousands of separate hues, while small differences in brightness are hard for the eye to detect. This is one way in which laser imaging system 100 exceeds the "Rayleigh Criterion" (a common measure of resolution) in its ability to see structures on the order of 0.1 to 0.2 micron size. Other aids in small feature detection are the improvement in resolution obtained with confocal optics, and the oversampling (overlapping images) performed by laser imaging system 100 that enables detection of features as small as 0.1 to 0.2 microns.

As an option, the laser optics can be used to obtain a fluorescence image of the wafer, detecting visible light in preselected wavelength bands. Fluorescence using white light or laser light in the same system is possible. Illuminating light of selected wavelengths will fluoresce certain materials, such as skin flakes or photoresist, the material emitting light at a longer wavelength. Suitable filters in front of the video camera block the illuminating radiation wavelength, but pass the longer wavelength, thus enabling identification of the material. This may also be done with the laser, fluorescing with a short wavelength, and placing a filter passing the longer wavelengths in front of the photo detector 212.

Polarized light images of objects or structures on the sample may be taken by illuminating the objects or structures with polarized white light and viewing the sample through a cross polarized filter. Optically active materials such as quartz will appear bright against the dark polarization extinction background. Optional brightfield/dark field objective lenses and illumination may be used to help locate particles and other defects on the wafer surface.

The same technique may be used with the confocal optics, by using linearly polarized light. Inserting a second quarter wave plate in the beam adds another 90 degree rotation, so that reflected light from the sample no longer passes to the detector, but light further rotated by passing through the optically active medium is allowed to pass and shows as a bright spot on the live laser scan.

A second major use of conventional microscope stations, different from the review or "revisit" function, is the more general defect detection function, where preselected sites on a wafer are inspected for efficacy of a previous process step. Laser imaging system 100 according to the invention is directly usable for this application, which faces exactly the same problems as defect imaging: decreasing size of objects of interest, a lack of resolution, and the need for three-dimensional imaging. The hardware required is exactly the same, as is the system control software. Only a variation in the application software is needed, so that predetermined inspection sites may be specified instead of defect map sites.

Overlay registration is another possible use of laser imaging system 100. Laser imaging system 100 can view photoresist layers on top of underlying structures to ascertain accuracy of placement of the photoresist layer with respect to features of the underlying structures.

Laser imaging system 100 can also be used to view through transparent (e.g., dielectric or glass) layers to allow determination of the vertical site of defects, or to provide some specialized inspection. For example, stress voids in metal layers below dielectric layers can be viewed. The depth of metal plugs in glass insulators can also be seen.

In its simplest mode, laser imaging system 100 works on opaque, diffusely scattering surfaces.

The laser imaging system according to the invention is unique in its capability for combining live video, live laser scan, three-dimensional imaging, wafer maps, and wafer surface profiles all on one screen. By selecting screens with different size and composition of windows the operator may view all the relative data needed for completion of his task.

The system according to the invention can be easily adapted for use in other materials science industries such as production of magnetic media, thin film heads, flat panel displays, etc. The necessary adaptations to laser imaging system 100 would include some software changes and some changes in the material handling system.

Appendix A accompanying this specification is a draft User's Manual for laser imaging system 100 and is herein incorporated by reference.

Various embodiments of the invention have been described. The descriptions are intended to be illustrative, not limitative. Thus, it will be apparent to one skilled in the art that certain modifications may be made to the invention as described without departing from the scope of the claims set out below.

We claim:

1. An imaging system comprising:
   means for inspecting a semiconductor die to determine the efficacy of a process previously performed on the semiconductor die, the means for inspecting comprising
   a multiline laser light source that emits laser light of a plurality of wavelengths,
   means for directing the laser light toward the semiconductor die, and
   means for measuring a first intensity of laser light reflected from the semiconductor die; and
   means for analyzing a defect on the semiconductor die to determine the nature and origin of the defect.

2. An imaging system as in claim 1, wherein the means for analyzing further comprises means for determining at least one material of which the defect is constituted.

3. An imaging system as in claim 1, wherein the means for analyzing further comprises means for determining at least one dimension of the defect.

4. An imaging system as in claim 1, wherein the means for analyzing further comprises means for determining a location of the defect on the semiconductor die.

5. An imaging system as in claim 1, wherein the laser emits one of said plurality of wavelengths at a second intensity, and wherein the means for inspecting further comprises a second filter that allows said one of said plurality of wavelengths to be transmitted to the semiconductor die with a third intensity inversely proportional to the second intensity.

6. An imaging system as in claim 1, further comprising:
   means for supporting the semiconductor die;
   means for isolating the semiconductor die within a region of the system, and wherein air within the region conforms to Class 1 cleanroom conditions.

7. An imaging system as in claim 6, further comprising means for remotely loading and unloading the semiconductor die onto and off of the means for supporting such that air within the region conforms to Class 1 cleanroom conditions.

8. An imaging system as in claim 1, wherein the imaging system can resolve features on the object as small as approximately 0.1 microns.

9. An imaging system as in claim 8, wherein the laser light source is an ultraviolet laser.

10. An imaging system as in claim 8, wherein images are rendered in false color.

11. An imaging system comprising:
a laser imaging means for imaging a surface of an object using laser light, the laser imaging means comprising
a laser light source that emits a beam of laser light;
a spatial filter for focusing the beam on a pinhole aperture;
a lens arranged between the pinhole aperture and the surface, the lens having a focal plane;
means for scanning the beam and directing the scanned beam toward the object through the lens; and
means for measuring the intensity of laser light reflected from the object and back through the lens and the pinhole aperture, wherein the measured intensity of laser light reflected from the object is at a maximum intensity when the surface lies in the focal plane of the lens; and
a white-light imaging means for imaging a surface of an object using white light, the white-light imaging means comprising
a white light source that emits white light;
means for directing the white light toward the object;
means for measuring the intensity of white light reflected from the object; and
a filter that prevents laser light from impinging upon the means for measuring the intensity of white light and allows white light to impinge upon the means for measuring the intensity of white light;
wherein the laser light imaging is performed at the same time as the white light imaging.

12. An imaging system as in claim 11, wherein one of the laser light or the white light is emitted at a first wavelength that causes fluorescence of a particular material in or on the object such that the one of the laser light or white light is reflected from the material at a second wavelength, and wherein the imaging system further comprises a filter that allows light of the second wavelength to pass through the filter, and prevents light of the first wavelength from passing through the filter.

13. An imaging system as in claim 11, wherein:
the means for imaging an object using laser light further comprises means for displaying the laser light image; and
the means for imaging an object using white light further comprises means for displaying the white light image.

14. An imaging system as in claim 13, wherein an image of the object can be displayed as a two-dimensional view of a surface of the object.

15. An imaging system as in claim 14, wherein an image of the object can be displayed as a two-dimensional view of a slice through the object.

16. An imaging system as in claim 15, wherein an image of the object can be displayed as a three-dimensional view of a surface of the object.

17. An imaging system as in claim 16, wherein at least two of the views can be displayed simultaneously.

18. An imaging system as in claim 11, wherein:
the laser light is polarized; and
the means for imaging an object using laser light further comprises means for allowing only light reflected from optically active material in or on the object to pass through to the means for measuring the intensity of laser light.

19. The imaging system of claim 11, wherein the scanning means comprises a resonant mechanical scanner.

20. An imaging system as in claim 11, wherein:
the white light is polarized; and
the means for imaging an object using white light further comprises means for allowing only light reflected from optically active material in or on the object to pass through to the means for measuring the intensity of white light.

21. An imaging system for detection or analysis of defects in or on an object, the system comprising:
means for producing light of a first polarity;
means for directing the light of a first polarity through a pinhole aperture and toward the object such that a portion of the light of a first polarity is reflected by a surface of the object;
a lens mounted between the pinhole aperture and the surface, the lens for focusing the light of a first polarity to a focal point on or within the object;
means for measuring the intensity of the light reflected from the object and back through the pinhole aperture, wherein the intensity of light reflected from the object is at a maximum intensity when the surface and the focal point of the lens are coincident;
means for changing the polarization of the light reflected by the object so that the polarization of the light reflected by the object is of a second polarity different than the first polarity;
means for filtering the reflected light so that the reflected light passing through the means for filtering has an intensity directly proportional to the distance between the focal point of the lens and the surface; and
means for analyzing the intensity of to create an image of the object.

22. A laser imaging system for imaging a surface of an object, the system comprising:
a laser light source that emits a beam of laser light, the beam focussed on a pinhole aperture;
a beam scanner configured to receive the beam from the pinhole aperture and output a scanned beam toward the surface;
a lens arranged between the beam scanner and the surface, the lens having a focal plane; and
a sensor generating an output signal proportional to the intensity of laser light reflected from the object and back through the lens, the beam scanner, and the pinhole aperture to impinge on the sensor, wherein the output signal of the sensor indicates a maximum intensity of reflected laser light when the surface lies in the focal plane of the lens.

23. The imaging system of claim 22, wherein the laser is a multiline laser light source that emits laser light at a plurality of wavelengths.

24. An imaging system as in claim 23, wherein the laser emits one of said plurality of wavelengths at a first intensity, and wherein the means for inspecting further comprises a filter that allows said one of said plurality to be transmitted to the semiconductor die with a second intensity inversely proportional to the first intensity.

25. An imaging system as in claim 23, wherein the beam travels along a first path between the laser and the surface, the system further comprising:
a beam splitter arranged in the first path of the beam between the laser and the lens, the beam splitter configured (1) to pass a first portion of light travelling along the first path and to reflect a second portion of light travelling along the first path so that the second portion of light travels along a second path not parallel to the first path, and (2) to pass a third portion of light travelling to the beam splitter along the second path and to reflect a fourth portion of light travelling to the beam splitter along the second path so that the fourth portion of light travels along the first path;

a white light source that emits white light along the second path to impinge the beam splitter and illuminate the surface;

a camera arranged to receive light travelling along the second path; and a filter arranged between the beam splitter and the camera, the filter preventing laser light from impinging upon the camera and allowing white light reflected from the surface and reflected by the beam splitter to impinge upon the camera.

26. An imaging system as in claim 22, further comprising:

a white light source that emits white light;

a reflective body for directing the white light toward the object; and a camera for white-light imaging, the camera configured to receive a portion of the white light reflected from the surface.

27. The imaging system of claim 26, wherein the laser light imaging and the white light imaging are performed simultaneously.

28. An imaging system as in claim 22, wherein the object is enclosed within a region of the system and wherein air within the region conforms to Class 1 cleanroom conditions.

29. An imaging system as in claim 22, wherein the beam scanner is a resonant mechanical scanner.

* * * * *